(12) United States Patent
Yamamoto et al.

(10) Patent No.: US 12,414,660 B2
(45) Date of Patent: Sep. 16, 2025

(54) INFORMATION COLLECTION APPARATUS AND APPARATUS ATTACHING METHOD

(71) Applicant: PARAMOUNT BED CO., LTD., Tokyo (JP)

(72) Inventors: Takeshi Yamamoto, Kanagawa (JP); Hirokazu Kobayashi, Kanagawa (JP); Junpei Kumagai, Kanagawa (JP); Kazutoshi Ohishi, Kanagawa (JP); Hiroshi Katayanagi, Kanagawa (JP); Keita Yamaguchi, Kanagawa (JP); Takeyoshi Obara, Kanagawa (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 78 days.

(21) Appl. No.: 18/683,791

(22) PCT Filed: Dec. 20, 2021

(86) PCT No.: PCT/JP2021/046987
§ 371 (c)(1),
(2) Date: Feb. 15, 2024

(87) PCT Pub. No.: WO2023/032242
PCT Pub. Date: Mar. 9, 2023

(65) Prior Publication Data
US 2024/0366045 A1 Nov. 7, 2024

(30) Foreign Application Priority Data
Aug. 30, 2021 (JP) .................................. 2021-140226

(51) Int. Cl.
*A47K 13/24* (2006.01)
*A61B 5/00* (2006.01)

(52) U.S. Cl.
CPC ............ *A47K 13/24* (2013.01); *A61B 5/6887* (2013.01)

(58) Field of Classification Search
CPC ...... E03D 9/00–9/16; A61B 5/06–5/22; A61B 5/6887; A61B 5/6889;
(Continued)

(56) References Cited

U.S. PATENT DOCUMENTS 10,575,830 B2   3/2020   Attar
11,129,599 B2   9/2021   Attar
(Continued)

FOREIGN PATENT DOCUMENTS

CN   112771233 A   *   5/2021   ............... E03D 9/00
JP   2012-017548 A       1/2012
(Continued)

OTHER PUBLICATIONS

International Search Report for PCT Application No. PCT/JP2021/046987, mailed on Mar. 8, 2022.

*Primary Examiner* — Lori L Baker
(74) *Attorney, Agent, or Firm* — WENDEROTH, LIND & PONACK, L.L.P.

(57) ABSTRACT

An information collection apparatus includes: a sitting sensor detecting that a user of a toilet bowl in a toilet is sitting on a toilet seat placed on the top surface of a rim of the bowl; an information collector collecting information about an excretion in the bowl; and a housing in which the sensor and the collector are placed. The apparatus includes: a bridge component bridging the inside of the rim and the outside of the rim by placing part of the component on the top surface of the rim of the bowl and sandwiching the rim; and a fitting being attached to an end of the component in a direction of the inside of the rim and attaching the housing. The apparatus includes a change mechanism changing the distance (Continued)

from the end to the housing in a direction along an inner wall forming the inside of the rim.

10 Claims, 11 Drawing Sheets

(58) Field of Classification Search
CPC .... A61B 10/0038; G01N 33/48–33/98; A47K 13/00–17/02; A61H 35/00
USPC .............................................................. 4/661
See application file for complete search history.

(56) References Cited

U.S. PATENT DOCUMENTS

| | | | | |
|---|---|---|---|---|
| 11,517,232 B1 * | 12/2022 | Robertson | ................. | G08G 5/26 |
| 11,679,386 B2 * | 6/2023 | Hall | ........................ | E03D 9/10 |
| | | | | 73/61.48 |
| 11,740,119 B2 * | 8/2023 | Hall | ...................... | G01G 19/44 |
| | | | | 4/240 |
| 11,759,065 B2 * | 9/2023 | Chung | .................. | A47K 13/10 |
| | | | | 4/246.1 |
| 11,786,224 B2 | 10/2023 | Attar | | |
| 12,345,702 B2 * | 7/2025 | Smith | .................. | G02B 21/365 |
| 2016/0278705 A1 | 9/2016 | Han et al. | | |
| 2018/0085098 A1 | 3/2018 | Attar | | |
| 2020/0100771 A1 | 4/2020 | Attar | | |
| 2021/0386408 A1 | 12/2021 | Attar | | |
| 2022/0049867 A1 * | 2/2022 | Rexach | ................... | F24F 7/003 |
| 2023/0160188 A1 * | 5/2023 | Waggott | ................ | E03C 1/126 |
| | | | | 4/222 |
| 2023/0200788 A1 | 6/2023 | Attar | | |
| 2025/0107714 A1 * | 4/2025 | Lane | ..................... | G16H 10/60 |

FOREIGN PATENT DOCUMENTS

| | | | | |
|---|---|---|---|---|
| JP | 2017-217228 A | | 12/2017 | |
| JP | 2018-510334 | | 4/2018 | |
| JP | 2018-528413 A | | 9/2018 | |
| JP | 6841366 B2 * | | 3/2021 | ............. A47K 13/24 |
| JP | 2021038640 A * | | 3/2021 | ............. G16H 10/60 |
| KR | 20220077990 A * | | 6/2022 | ............... A61F 5/442 |
| WO | WO-2021040015 A1 * | | 3/2021 | ............ G01N 21/255 |
| WO | WO-2021055681 A1 * | | 3/2021 | ............. G01G 19/52 |
| WO | 2021/060212 A1 | | 4/2021 | |

* cited by examiner

INFORMATION COLLECTION APPARATUS AND APPARATUS ATTACHING METHOD

This application is a National Stage Entry of PCT/JP2021/046987 filed on Dec. 20, 2021, which claims priority from JP Patent Application 2021-140226 filed on Aug. 30, 2021, the contents of all of which are incorporated herein by reference, in their entirety.

TECHNICAL FIELD

The present disclosure relates to an information collection apparatus and an apparatus attaching method.

BACKGROUND ART

Patent Literature 1 describes a toilet seat apparatus including a toilet seat placed above a toilet bowl, an image sensor being provided on the back side of the toilet seat and capturing an image of an internal space of the toilet bowl at excretion, and an unexpected appearance prevention unit preventing appearance of a human body in a target image captured by the image sensor. Patent Literature 1 further describes a technology for performing, in cooperation with a sitting sensor, such as a load sensor, detecting a time when a user sits on a toilet seat, control in such a way as to cause the image sensor to capture an image of the internal space of the toilet bowl when sitting is detected.

CITATION LIST

Patent Literature

[Patent Literature 1] International Patent Publication No. WO 2021/060212

SUMMARY OF INVENTION

However, the toilet seat apparatus described in Patent Literature 1 is an apparatus in which the image sensor and an illumination unit for image capture of an excretion are fixed on the back side of the toilet seat; and, depending on placement intervals of projecting parts of elastic members on the back side of the toilet seat, the members coming in contact with the top surface of a rim of the toilet bowl, the same image sensor and the same illumination unit may not be attached. The reason is that the placement intervals vary by the type of available toilet seat, and depending on the placement intervals, the image sensor and the illumination unit interfere with the aforementioned projecting part. Therefore, the toilet seat apparatus described in Patent Literature 1 requires a dedicated product to be developed for each type of already available toilet bowl and/or toilet seat for image capture of an excretion.

Furthermore, for recognition of an excretion including an evacuation at an outlet, an apparatus needs to be installed in the rear part of a toilet bowl. However, it is difficult to install the toilet seat apparatus described in Patent Literature 1 at such a position, and it is difficult to capture an image of an excretion including an evacuation at the outlet.

An object of the present disclosure is to provide an information collection apparatus that can be attached to a toilet bowl for any toilet bowl and any toilet seat that are already available and can collect information about an excretion including an evacuation at an outlet, and an apparatus attaching method.

An information collection apparatus according to a first aspect of the present disclosure includes: a sitting sensor configured to detect that a user of a toilet bowl in a toilet is sitting on a toilet seat placed on a top surface of a rim of the toilet bowl; and an information collection unit configured to collect information about an excretion in the toilet bowl. The information collection apparatus includes: a housing in which the information collection unit and the sitting sensor are placed; and a bridge component configured to bridge an inside of a rim of the toilet bowl and an outside of the rim by placing part of the bridge component on a top surface of the rim and sandwiching the rim. The information collection apparatus includes: a fitting configured to be attached to an end of the bridge component in a direction of an inside of the rim and attach the housing; and a change mechanism configured to change a distance from the end to the housing in a direction along an inner wall forming an inside of the rim.

An apparatus attaching method according to a second aspect of the present disclosure includes a step of bridging an inside of a rim of a toilet bowl in a toilet and an outside of the rim by placing part of a bridge component on a top surface of the rim and sandwiching the rim by the bridge component. The apparatus attaching method includes a step of attaching a fitting to an end of the bridge component in a direction of an inside of the rim. The apparatus attaching method includes a step of attaching, to the fitting, a housing in which a sitting sensor configured to detect that a user of the toilet bowl is sitting on a toilet seat placed on a top surface of the rim and an information collection unit configured to collect information about an excretion in the toilet bowl are placed. The apparatus attaching method includes a step of changing, by using a change mechanism, a distance from the end to the housing in a direction along an inner wall forming an inside of the rim. The change mechanism is a mechanism fixing the bridge component to the fitting and fixing the housing to the fitting. The change mechanism is a mechanism changing the distance by using, as the fitting to be fixed, a fitting selected from among a plurality of fittings with varying lengths in a direction along the inner wall.

An apparatus attaching method according to a third aspect of the present disclosure includes: a step of bridging an inside of a rim of a toilet bowl in a toilet and an outside of the rim by placing part of a bridge component on a top surface of the rim and sandwiching the rim by the bridge component; and a step of attaching a fitting to an end of the bridge component in a direction of an inside of the rim. The apparatus attaching method includes a step of attaching, to the fitting, a housing in which a sitting sensor configured to detect that a user of the toilet bowl is sitting on a toilet seat placed on a top surface of the rim and an information collection unit configured to collect information about an excretion in the toilet bowl are placed. The apparatus attaching method includes a step of changing, by using a change mechanism, a distance from the end to the housing in a direction along an inner wall forming an inside of the rim. The change mechanism is a sliding mechanism sliding a position of the housing relative to the end in a direction along the inner wall.

An apparatus attaching method according to a fourth aspect of the present disclosure includes a step of bridging an inside of a rim of a toilet bowl in a toilet and an outside of the rim by placing part of a bridge component on a top surface of the rim and sandwiching the rim by the bridge component. The apparatus attaching method includes a step of attaching a fitting to an end of the bridge component in a direction of an inside of the rim. The apparatus attaching method includes a step of attaching, to the fitting, a housing in which a sitting sensor configured to detect that a user of the toilet bowl is sitting on a toilet seat placed on a top surface of the rim and an information collection unit configured to collect information about an excretion in the toilet bowl are placed. The apparatus attaching method includes a step of changing, by using a change mechanism, a distance from the end to the housing in a direction along an inner wall forming an inside of the rim. The change mechanism is an extension-shortening mechanism being provided in the fitting and extending and shortening a length in a direction along the inner wall.

The present disclosure can provide an information collection apparatus that can be attached to a toilet bowl for any toilet bowl and any toilet seat that are already available and can collect information about an excretion including an evacuation at an outlet, and an apparatus attaching method.

EXAMPLE EMBODIMENT

Example embodiments will be described below with reference to drawings. Note that, in the example embodiments, the same or equivalent components may be given the same signs, and redundant description thereof is omitted as appropriate.

First Example Embodiment

Figure 1:
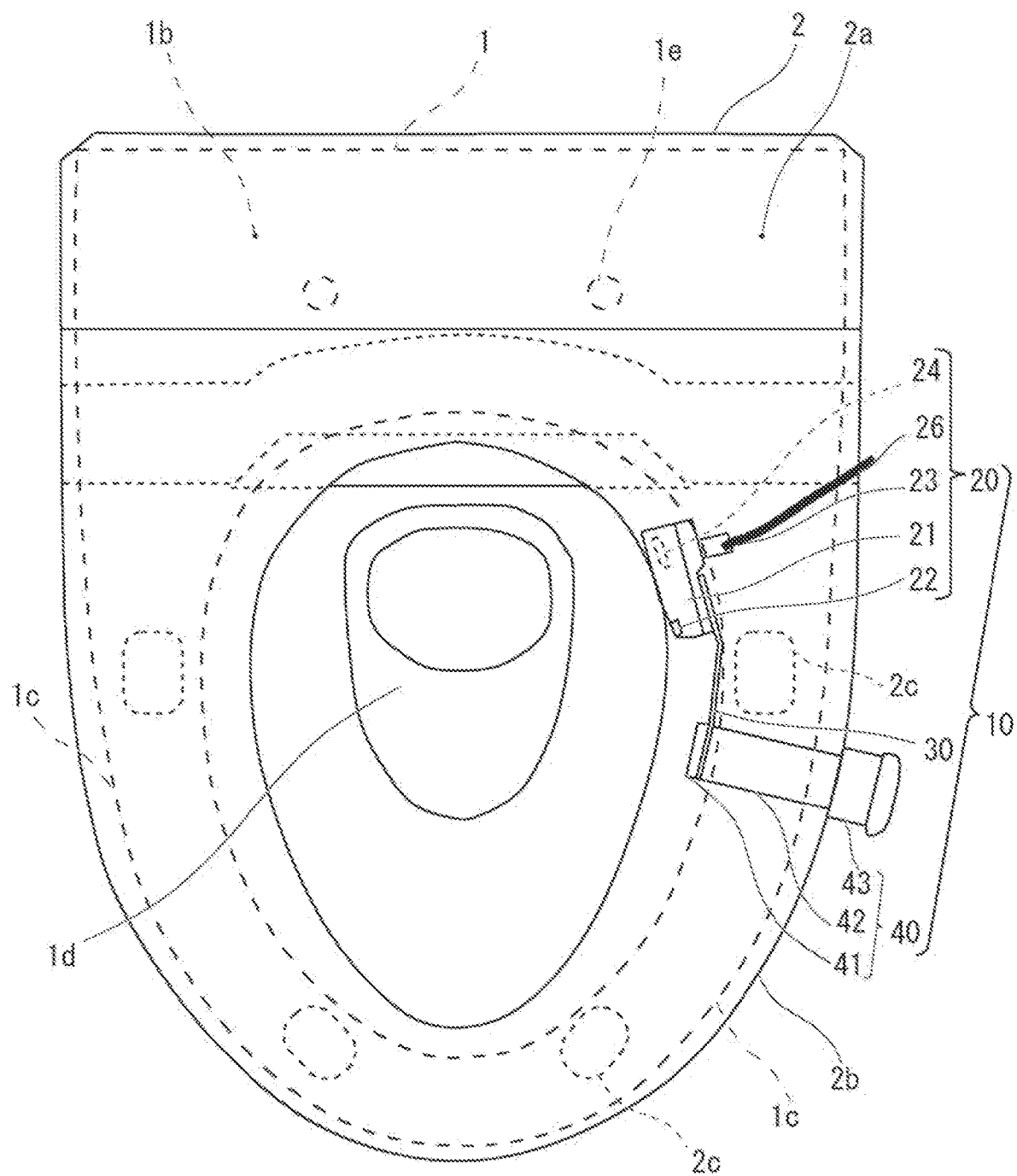
FIG. 1 is a top view illustrating a configuration example of a toilet bowl in which an information collection apparatus according to a first example embodiment is installed.
Figure 2:
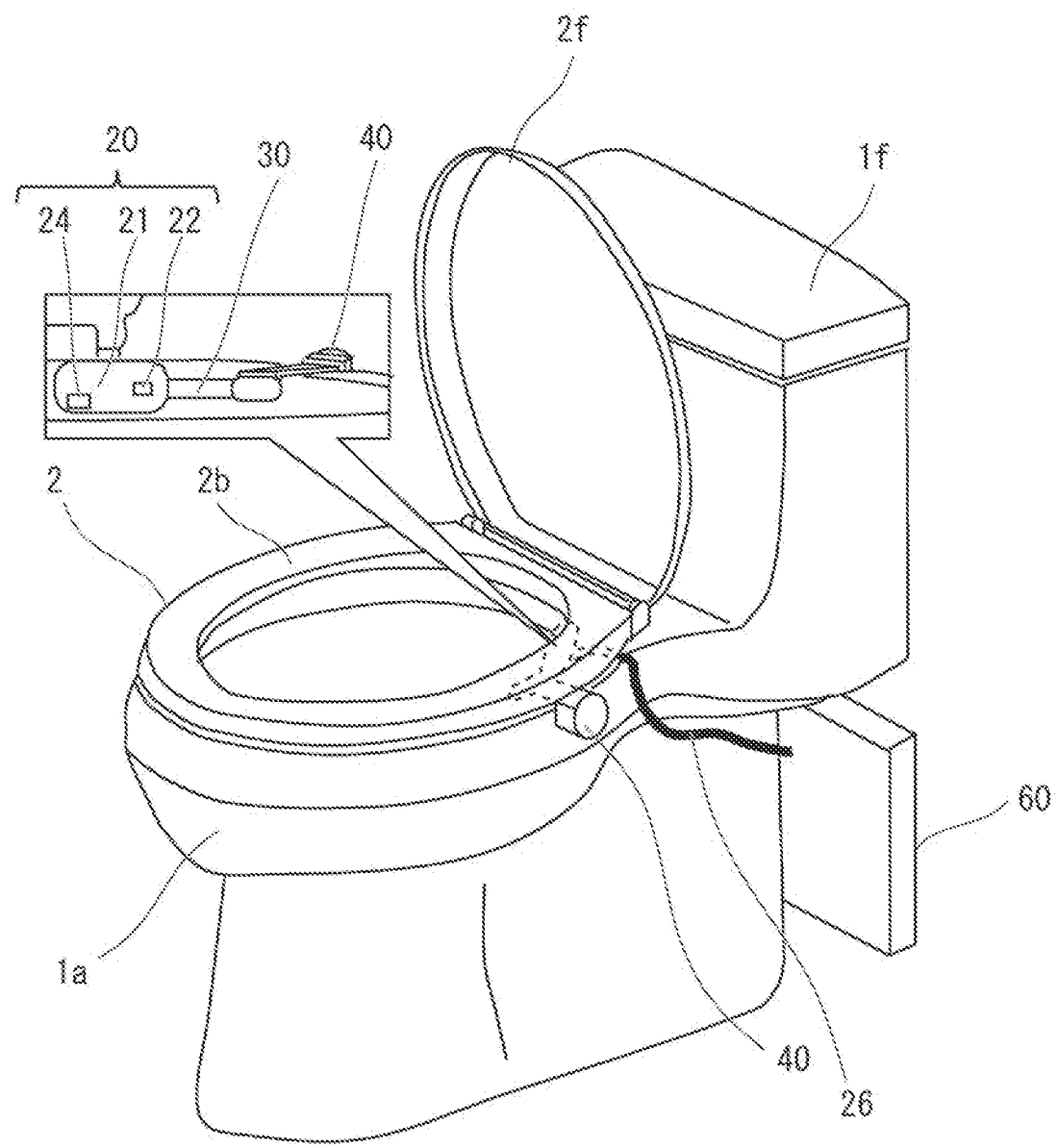
FIG. 2 is a perspective view illustrating a configuration example in which a lid and a water tank are added to the toilet bowl in FIG. 1.

A first example embodiment will be described with reference to FIG. 1. FIG. 1 is a top view illustrating a configuration example of a toilet bowl in which an information collection apparatus according to the first example embodiment is installed, and FIG. 2 is a perspective view illustrating a configuration example in which a lid and a water tank are added to the toilet bowl in FIG. 1.

As illustrated in FIG. 1, the information collection apparatus 10 according to the present example embodiment is installed in a toilet bowl 1 in a toilet and may include a housing 21, a sitting sensor 22, an information collection unit 24, a fitting 30, a bridge component (bridge member) 40, and a control unit (unillustrated). The control unit can control the sitting sensor 22 and the information collection unit 24.

The toilet bowl 1 may include a rim 1c for forming a reservoir part 1d between sides thereof and may also include a plane part 1b continuing from the rim 1c. A toilet seat 2 may be installed on the plane part 1b. For example, an attachment part 1e formed of a recessed part or a hole for attaching the toilet seat 2 is formed on the plane part 1b, and the toilet seat 2 is provided with a projecting part in a shape engaging with the attachment part 1e. Alternatively, the toilet seat 2 can be attached to the toilet bowl 1 with a rod-shaped member in a shape engaging with the attachment part 1e interposed therebetween. Note that, as illustrated in FIG. 2, the toilet bowl 1 may be provided with a water tank 1f.

The toilet seat 2 can be thus attached to the plane part 1b. The toilet seat 2 may include an attachment part 2a attached to a position related to the plane part 1b, and a toilet seat body 2b attached to the attachment part 2a by a hinge in such a way as to allow contact with and separation from the top surface of the rim 1c of the toilet bowl 1. Furthermore, the toilet seat 2 may include a projecting part 2c attached on the back side of the toilet seat body 2b (the back side of the seat surface). In other words, the toilet seat 2 may be openably and closably installed in such a way as to come in contact with the top surface of the rim 1c at the projecting part 2c when a user uses the toilet seat 2. Note that the toilet bowl 1 and the toilet seat 2 are not limited to those illustrated and the shapes thereof are not considered relevant. Further, the shape of the toilet seat 2 installable on the toilet bowl 1 is not limited to one, and an installer may select and install an appropriate toilet seat. The projecting part 2c may formed in such a way as to include an elastic member, such as a rubber, and may also be referred to as a rubber foot or the like. Further, as illustrated in FIG. 2, the toilet seat 2 may include a lid 2f, and the lid 2f can be openably and closably attached to the toilet seat body 2b.

The housing 21 is a housing in which the sitting sensor 22 and the information collection unit 24 are placed by incorporation of the entire sitting sensor 22 and the entire information collection unit 24 or a part thereof such as a part other than the sensor surface, and the placement part 23 placed on the top surface of the rim 1c of the toilet bowl 1 is also placed in the housing 21. The housing 21 is a housing placed inside the toilet bowl 1 and therefore is hereinafter referred to as an inner housing 21. Further, the inner housing 21 may also include an illumination unit, such as light emitting diode (LED) for illumination, for illuminating an excretion being a collection target by the information collection unit 24.

At least the inner housing 21, the sitting sensor 22, and the information collection unit 24 constitute a sensor box (sensor unit) 20. Since the information collection unit 24 collecting information about an excretion (excretion information) of a care recipient or the like is mounted in the sensor box 20, the sensor box 20 may also be referred to as an excretion detection unit (excretion information collection unit), a sanitary sensor (sanitary use record sensor), or a toilet sensor. Further, the information collection apparatus 10 itself may be referred to as a sanitary sensor or a toilet sensor.

The sitting sensor 22 detects that a user of the toilet bowl 1 in a toilet is sitting on the toilet seat 2 placed on the top surface of the rim 1c of the toilet bowl 1. While the following description is based on the premise that the sitting sensor 22 is a distance sensor, for example, the sitting sensor 22 may be a weight sensor placed on the placement part 23 between the back side of the toilet seat 2 and the top surface of the rim 1c of the toilet bowl 1.

The sitting sensor 22 may be a distance sensor and measures the distance to an object located in a direction of the inside of the toilet seat 2. The measurement may be performed at least when the toilet seat 2 installed on the toilet bowl 1 is placed on the top surface of the rim 1c of the toilet bowl 1. For example, an infrared sensor, an ultrasonic sensor, or an optical sensor may be employed as the distance sensor. When an optical sensor is employed, a transmission-reception element may be placed in the distance sensor in such a way as to enable transmission and reception of light (not being limited to visible light) from a hole provided in the inner housing 21. The transmission-reception element may include a transmission element and a reception element separately or may include the elements in an integrated manner.

An object being a measurement target of the distance sensor is the buttocks of a user, and, as a matter of course, an object being a measurement target does not exist or the object is a distant wall, a ceiling, or the like when a user does not use the toilet. A ranging method employed in the distance sensor is not considered relevant, and the distance sensor is not limited to an optical distance sensor. Further, the distance sensor may also be referred to as a range sensor. Note that a switch for detecting that the toilet seat 2 is placed on the top surface of the rim 1c by depression by the back side of the toilet seat 2 (or for performing the detection and operating the sitting sensor 22) may be provided in the inner housing 21 where the distance sensor is placed.

The information collection unit 24 collects information about an excretion in the toilet bowl 1. For example, the information collection unit 24 may be an image capture apparatus collecting a content of an excretion, such as the shape and/or the color of the excretion, through an optical lens, or a distance sensor optically measuring a distance. FIG. 2 gives an example of placing, as the information collection unit 24, a camera in the inner housing 21 in an excreting direction of an excretion. The excretion information may refer to information indicating a content of excretion and, in a simpler example, may refer to information indicating that the excretion is feces (stool) or pee (urine). The excretion information may also include other types of information such as information indicating the color of an excretion and the shape of an excretion when the excretion is a solid matter. The information collection unit 24 may be configured to simply detect and collect existence of excretion as information about an excretion.

The information collection unit 24 may have a region including a reservoir part of the toilet bowl (an excretion area) as a collection area, and the excretion area may also be referred to as an expected excretion area. By installing the information collection unit 24 in such a way as to include such an excretion area into an image capture area, captured image data include an excretion and the like as subjects. The information collection unit 24 is placed in such a way as to be able to collect information from a gathering part (a region where an excretion is excreted) of the toilet bowl 1 by, for example, exposing the information collection surface of the information collection unit 24 from an opening of the inner housing 21. For example, a lens surface in a case of a camera and a detection surface in a case of a sensor fall under the aforementioned information collection surface. As a matter of course, the aforementioned excretion area is preferably set to an area in which a user does not appear, and the information collection unit 24 is preferably installed in such a way that the lens and the like are not visible to the user.

Inclusion of the information collection unit 24 enables collection of information about an excretion excreted by a user of a toilet without the need for gathering information from the user through an inquiry. Note that the sitting sensor 22 also collects information indicating a sitting state and therefore may be considered part of the information collection unit.

Further, FIG. 1 and FIG. 2 give an example of the control unit being provided outside the sensor box 20 and being connected to a cord 26 drawn from the inner housing 21. The cord 26 is routed through a region where the projecting part 2c of the toilet seat body 2b does not exist and is taken out of the toilet bowl 1. Note that wireless communication may be used in place of the cord 26.

The aforementioned control unit is connected to the sitting sensor 22 and the information collection unit 24 by wired or wireless communication and controls the sitting sensor 22 and the information collection unit 24. While the control unit may be provided in the inner housing 21, in other words, be included in the sensor box 20, the control unit may also be provided in the outer housing 43 or another outer housing provided to be placed outside the toilet bowl 1.

For example, the aforementioned control unit may be provided by a central processing unit (CPU), a work memory, and a nonvolatile storage device in which a program is stored. For example, the program may be a program for causing the CPU to execute processing such as determination of sitting on or leaving the seat and collection of excretion information. Further, for example, the aforementioned control unit may also be provided by an integrated circuit.

The fitting 30 and the bridge component 40 are components attaching the inner housing 21 to the toilet bowl 1. While the fitting 30 may be metal, in other words, may be a metal fitting, the material thereof is not considered relevant. Further, the material of the bridge component 40 is basically not considered relevant either.

The bridge component 40 is a component bridging the inside of the rim 1c of the toilet bowl 1 and the outside of the rim 1c by placing part of the bridge component 40 on the top surface of the rim 1c and sandwiching the rim 1c, and, for example, may be a clamping mechanism. The fitting 30 is attached to an end 41 of the bridge component 40 in a direction of the inside of the rim 1c and is a component attaching the inner housing 21. The inner housing 21 can be attached to the toilet bowl 1 by the bridge component 40 and the fitting 30.

Then, the information collection apparatus 10 according to the present example embodiment includes a change mechanism changing the distance from the end (tip) 41 to the inner housing 21 in a direction along an inner wall forming the inside of the rim 1c. Note that whether the aforementioned inner wall is a curved surface (an elliptic toilet bowl) or a flat surface (a rectangular toilet bowl), the distance may be defined as a distance along the surface or may be defined as a direct distance.

The following change mechanism is given as an example of the aforementioned change mechanism and will be described in the present example embodiment. Specifically, the aforementioned change mechanism is a mechanism fixing the bridge component 40 to the fitting 30 and fixing the inner housing 21 to the fitting 30. Then, the aforementioned change mechanism is a mechanism changing the aforementioned distance by using, as the fitting 30 to be fixed, a fitting selected from among a plurality of fittings with varying lengths in the direction along the aforementioned inner wall. In other words, the change mechanism changes the aforementioned distance by selecting a fitting with a length that fits the toilet bowl 1 and the toilet seat 2 from among fittings with a plurality of lengths and attaching the selected fitting.

Figure 3:
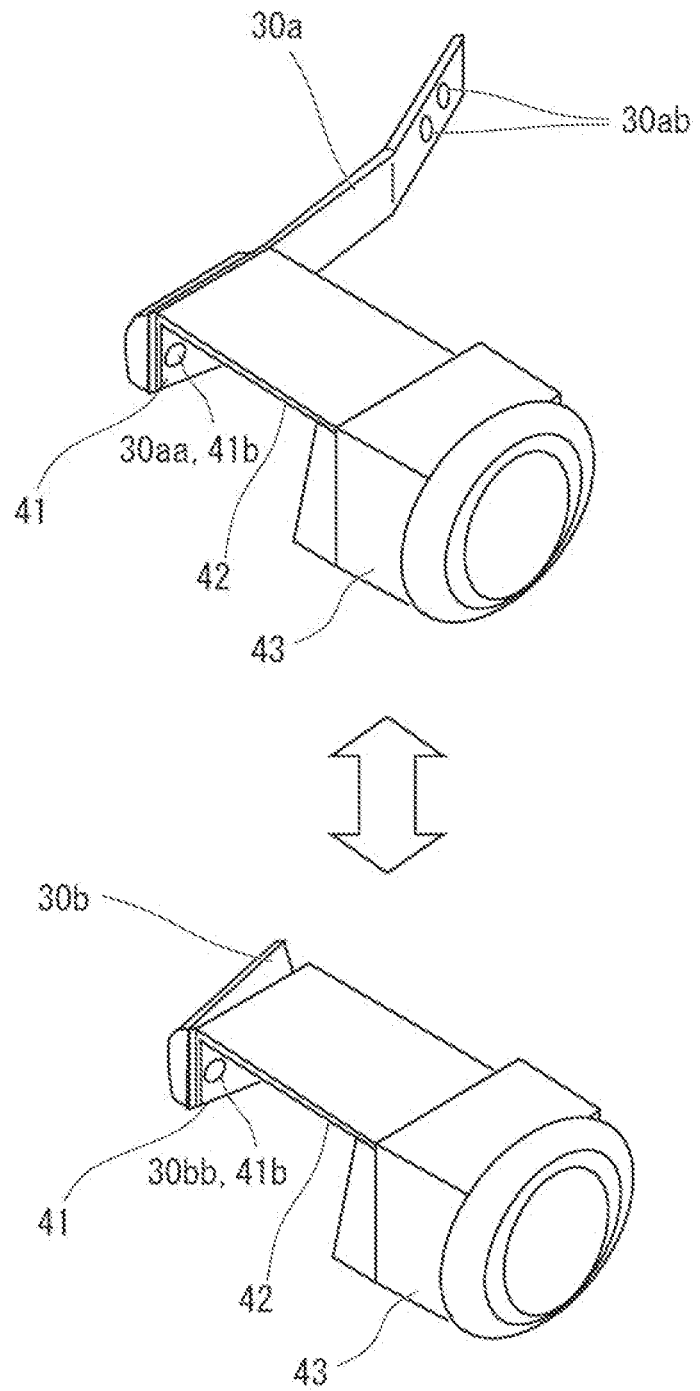
FIG. 3 is a perspective view illustrating an example of a fitting in the information collection apparatus in FIG. 1.
Figure 4:
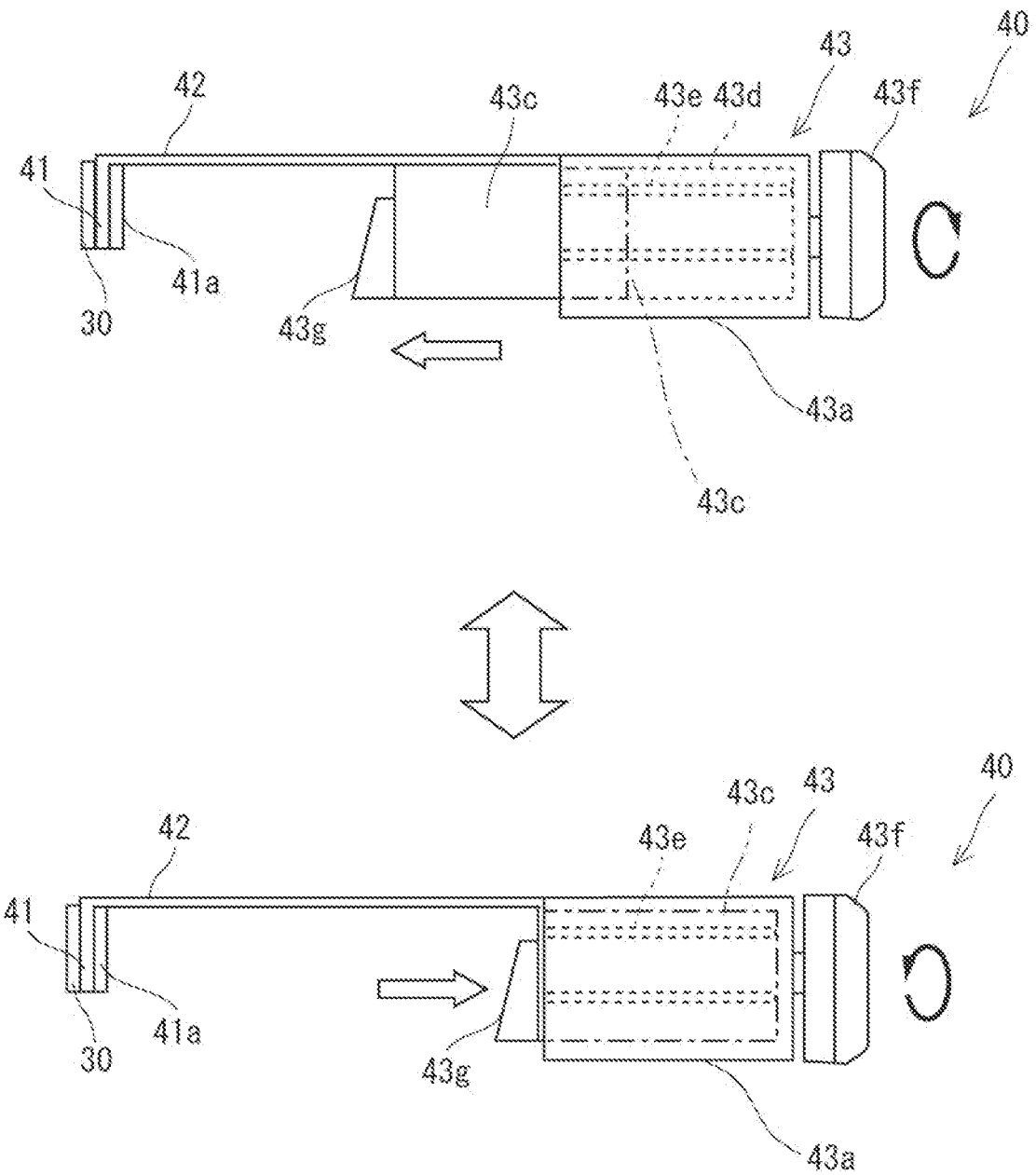
FIG. 4 is a side view illustrating an example of the fitting in the information collection apparatus in FIG. 1.

An example of the fitting 30 and the bridge component 40 constituting the aforementioned change mechanism applicable to the information collection apparatus 10 will be described with reference to FIG. 3 and FIG. 4. FIG. 3 is a perspective view illustrating an example of the fitting 30 and the bridge component 40 in the information collection apparatus 10 in FIG. 1. FIG. 4 is a side view illustrating an example of the fitting 30 and the bridge component 40 in the information collection apparatus 10.

The bridge component 40 may be a metal fitting for fixing the sensor box 20 to the rim 1c of the toilet bowl 1 and, as illustrated in the upper diagram and the lower diagram in FIG. 3, may include a tip 41, a bridging part 42, and an outer housing 43. The outer housing 43 is provided with a handle (a dial knob 43f to be described later) and is fixed by clamping the rim 1c of the toilet bowl 1 by turning the handle. An example of a fixing clamping mechanism for the clamping will be described later with reference to FIG. 4. Further, as illustrated in the upper diagram in FIG. 3, the tip 41 is provided with a fixing part 41b for fixing a fitting 30a with a screw or the like, and, as illustrated in the lower diagram in FIG. 3, the fixing part 41b also allows fixing of a fitting 30b with a different length with a screw or the like.

For example, the fitting 30 may be a plate-shaped or rod-shaped member; and one end of the fitting 30 is attached to the tip 41 of the bridge component 40, and the other end is attached to the inner housing 21. Assuming the shape of the inside of the rim 1c of the toilet bowl 1 (roundness in the example in FIG. 1), the shape of the fitting 30 in the longitudinal direction may have a similar shape. Specifically, the fitting 30 includes an extension part shaped along the inner wall forming the inside of the rim 1c, and the inner housing 21 may be attached to the tip of the extension part.

Two or more fittings 30 are prepared in the present example embodiment. While the fitting 30a and the fitting 30b are described as a long type and a short type, respectively, three or more types of fittings 30 may also be previously prepared. Each of the fittings 30a and 30b is an attachment for connecting the sensor box 20 to the bridge component 40. An installer may select either one of the long-type fitting 30a and the short-type fitting 30b and can connect the sensor box 20 to the bridge component 40 by using the selected fitting.

The fitting 30a is provided with a fixing part 30aa, such as a hole, for fixing the bridge component 40 at the end 41 and is provided with a fixing part 30ab, such as a hole, for fixing the inner housing 21. On the other hand, the short-type fitting 30b is provided with a fixing part 30bb, such as a hole, for simultaneously fixing the end 41 of the bridge component 40, and the inner housing 21.

An example of the fixing clamping mechanism in the bridge component 40 will be described.

As illustrated in FIG. 4, the fixing clamping mechanism may include a connecting member such as a connecting plate bent in an L-shape, a sliding member 43c for clamping the rim 1c of the toilet bowl 1 with the tip 41, and a storage part 43d for sliding the sliding member 43c in the horizontal direction. The tip 41 and the bridging part 42 may be formed by bending a connecting member such as a connecting plate into an L-shape. The tip 41 is a member for being hooked to the rim 1c of the toilet bowl 1. The outer housing 43 includes a housing body 43a, and the housing body 43a also serves as a cover protecting the fixing clamping mechanism such as a fixing metal fitting. The opposite side of the bridging part 42 from the tip 41 is fixed to the housing body 43a.

Further, the fixing clamping mechanism may include one or a plurality of slide grooves 43e in the storage part 43d in such a way as to be able to move the sliding member 43c in the horizontal direction between the states in the upper diagram and the lower diagram in FIG. 4. Further, in order to adjust and fix an amount of the movement, the dial knob 43f is provided in the fixing clamping mechanism in such a way as to be rotatable around the sliding direction. Employment of the dial knob 43f enables easy attachment and detachment merely by adjustment by turning the dial with a weak force without requiring a tool. Further, use of a knob with a torque limiter as the dial knob 43f facilitates confirmation of normal installation. Note that an adjustment knob and a fixing member may be provided in place of the dial knob 43f.

Further, an elastic member 43g for clamping the rim 1c may be provided on the toilet bowl 1 side (the tip 41 side) of the sliding member 43c, and an elastic member 41a for clamping the rim 1c may also be provided on the housing body 43a side of the tip 41. The shape and the material of the elastic members 43g and 41a have only to allow firm clamping of the rim 1c without misalignment at the contact part with the rim 1c. Further, the distance between the two members has only to allow a maximum length assumed as the rim 1c to be secured when the sliding member 43c is fully stored in the storage part 43d (the state in the lower diagram in FIG. 4).

The bridging part 42 is a part bridging the inside of the rim 1c of the toilet bowl 1 and the outside of the rim 1c in a state of placing at least part of the bridging part 42 on the top surface of the rim 1c and sandwiching the rim 1c. The bridging part 42 is a part connecting the tip 41 to the outer housing 43 and being placed on the top surface of the rim 1c and may also be referred to as a horizontal part or a connecting part. Thus, the bridge component 40 is fixed to the rim 1c at the tip 41 and the outer housing 43 by adjusting the distance to the inside of the rim 1c with the bridging part 42 interposed therebetween and clamping the rim 1c. Thus, the bridge component 40 can adjust to the width of the rim 1c.

Further, while FIG. 4 gives an example of fixing the fitting 30 (the fitting 30a or 30b in this example) on the opposite side of the tip 41 from the housing body 43a, the fitting 30 may be fixed between the tip 41 and the elastic member 41a. In other words, the tip 41 may be provided with a structure allowing attachment of the fitting 30 attached with the inner housing 21.

Thus, the inner housing 21 in the information collection apparatus 10 can be securely fixed and installed regardless of the shape of the toilet bowl 1 such as the shape of the rim 1c. Note that while an example of main components of the fixing clamping mechanism being provided in the outer housing 43 is given, the shape and the component of the fixing clamping mechanism is not considered relevant as long as the mechanism allows such fixing. Further, while an example of using a C-clamp as the fixing clamping mechanism is given in FIG. 4, the mechanism is not limited thereto.

Further, employment of such a fixing clamping mechanism enables a smaller size, a smaller number of grooves, easy wiping, and a reduced cleaning time. Further, while the fixing clamping mechanism is desirably formed of metal excluding the elastic members 43g and 41a in terms of strength, for example, the storage part 43d and/or the sliding member 43c may be formed of another material such as resin.

As can be understood from the aforementioned description, attachment/detachment of mainly the inner housing 21 in the information collection apparatus 10 to/from the toilet bowl 1 can be performed by rotating the dial knob 43f clockwise/counterclockwise. At attachment, the fitting 30 is attached to the tip 41, the tip 41 of the bridging part 42 (the elastic member 41a in practice) is hooked to the rim 1c of the toilet bowl 1 from the state as illustrated in the lower diagram in FIG. 4, and then the dial knob 43f is rotated counterclockwise for fixing. Thus, the distance between the sliding member 43c and the tip 41 is shortened and installation can be performed as illustrated in the upper diagram in FIG. 4. Attachment of the fitting 30 to the inner housing 21 may be performed in advance or may be performed after fixing by the aforementioned rotation. At detachment, by rotating the dial knob 43f clockwise for release of fixing, fixing of the structure is released as the state illustrated in the lower diagram in FIG. 4, and detachment is enabled. Use of a knob with a torque limiter as the dial knob 43f particularly facilitates normal installation confirmation of attachment and detachment.

As described above, by including such a fixing clamping mechanism, the information collection apparatus 10 can be simply installed in and detached from a wide variety of commercially available toilet bowls 1 without using a tool and without replacing a toilet bowl in a toilet with a dedicated product. Further, by rotating the dial knob 43f, the sensor box 20 can be readily attached to and detached from the toilet bowl 1 by a strong force even when a force applied in an opening-closing operation is weak. Further, an apparatus series does not need to be added for each type of toilet bowl, and an apparatus vendor can reduce the administrative cost. Further, by including the fixing clamping mechanism as described above, for example, easy detachment and reinstallation can be performed when the toilet bowl 1 is cleaned. Further, by including a fixing clamping mechanism as described above, a cleaner in a state of wearing gloves for cleaning can readily perform detachment and reinstallation, and efficiency of cleaning work can be improved.

While some types of toilets include a handrail beside a toilet bowl, the information collection apparatus 10 can be installed in such types without particularly reducing the width of the outer housing 43. Further, for example, a control box including the aforementioned control unit can be separately placed on the side at the rear of the toilet bowl 1, and therefore, a component attached to the toilet bowl 1 can be installed without particularly reducing the width.

Further, without being limited to the above, examples of the bridge component 40 may include a clamping mechanism installed between the side of the toilet bowl 1 and a part corresponding to the outer housing 43. The clamping mechanism may be a mechanism coming in contact with the side of the toilet bowl 1 and a surface of the part corresponding to the outer housing 43 on the toilet bowl 1 side and adjusting the length therebetween.

Next, an example of a method for attaching the information collection apparatus 10 by the fitting 30 and the bridge component 40 will be described with additional reference to FIG. 5 to FIG. 8. FIG. 5 to FIG. 8 are perspective views illustrating a scene in which the information collection apparatus 10 is installed in the toilet bowl 1.

The apparatus attaching method according to the present example embodiment includes a bridge step, a first attachment step, a second attachment step, and a change step as follows.

The bridge step bridges the inside of the rim 1c and the outside of the rim 1c by placing part of the bridge component 40 on the top surface of the rim 1c of the toilet bowl 1 in a toilet and sandwiching the rim 1c by the bridge component 40. The first attachment step attaches the fitting 30 to the end 41 of the bridge component 40 in a direction of the inside of the rim 1c. The second attachment step attaches the inner housing 21 in which the sitting sensor 22 and the information collection unit 24 are placed to the fitting 30. The change step changes, by using the aforementioned change mechanism (in other words, by selecting a fitting 30 to be used), the distance from the end 41 to the inner housing 21 in the direction along the inner wall forming the inside of the rim 1c.

The order of the steps is not considered relevant except that the change step is executed before the first attachment step and the change step is executed before the second attachment step at final attachment. Note that when a suitable fitting 30 is originally selected, the change step may not be performed as a result.

A specific example of the order of the steps will be described.

Figure 5:
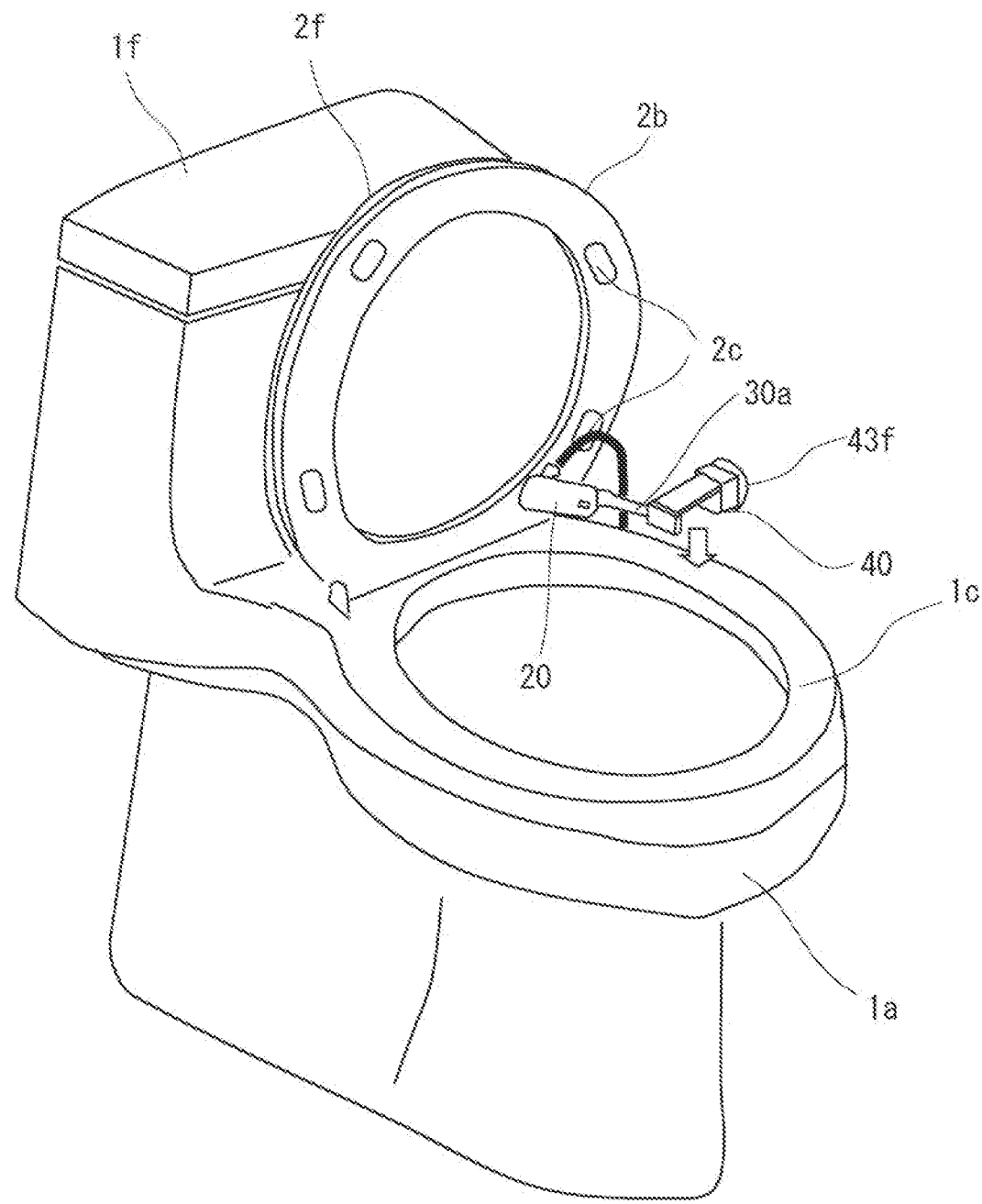
FIG. 5 is a perspective view illustrating a scene in which the information collection apparatus in FIG. 1 is installed in the toilet bowl.
Figure 6:
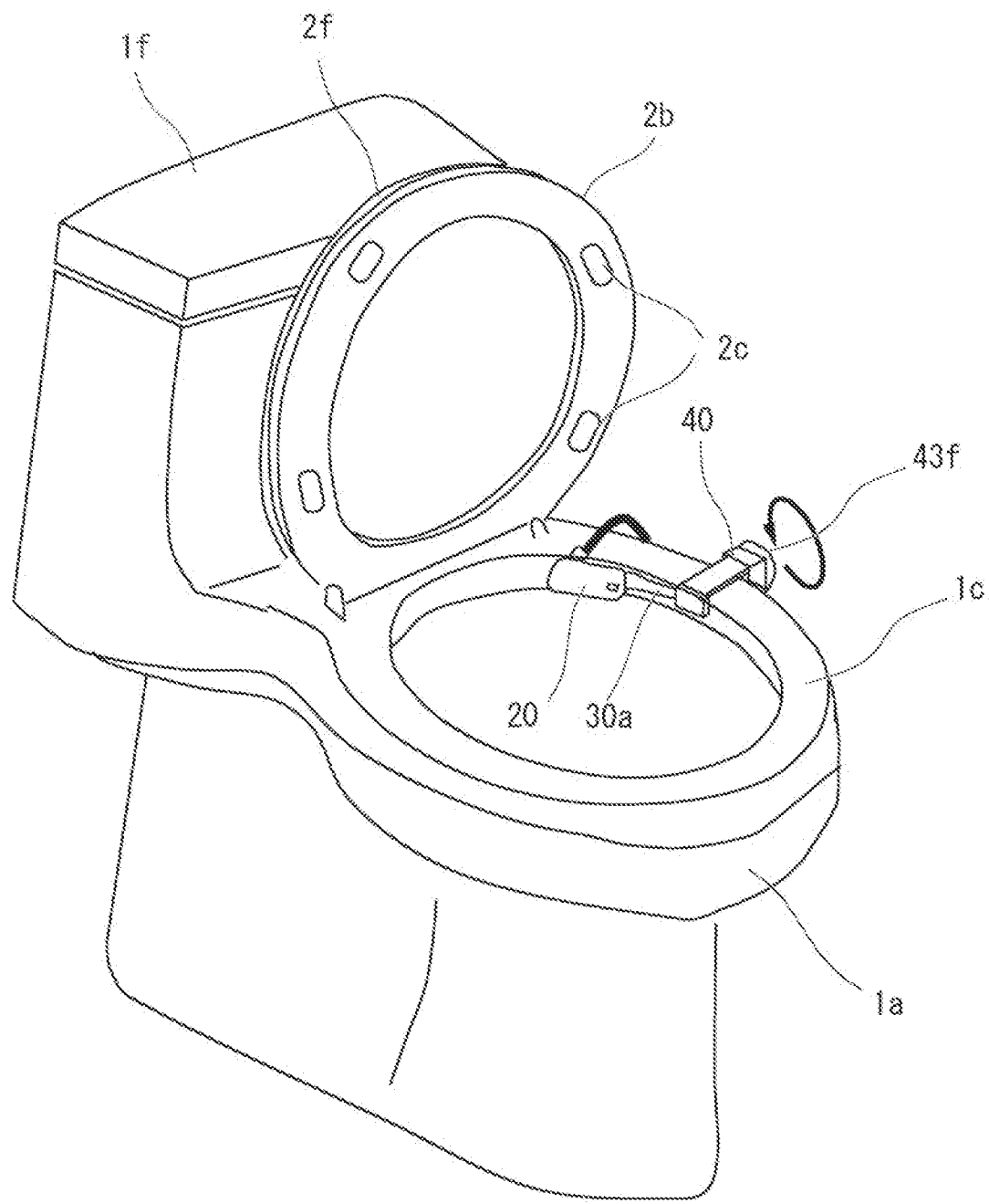
FIG. 6 is a perspective view illustrating a scene in which the information collection apparatus in FIG. 1 is installed in the toilet bowl.

First, as illustrated in FIG. 5, the bridge component 40 is mounted on the toilet bowl 1 in such a way that the sensor box 20 is aligned to the position of the rear side of the inside of the toilet bowl 1 in a state of the sensor box 20 being fixed to the bridge component 40 by the fitting 30a (see an outlined arrow in FIG. 5). Next, as illustrated in FIG. 6, after the mounting, a usable width of the bridging part 42 is reduced by turning the handle (dial knob 43f) of the bridge component 40, and the bridge component 40 is fixed by clamping the rim 1c of the toilet bowl 1.

Figure 7:
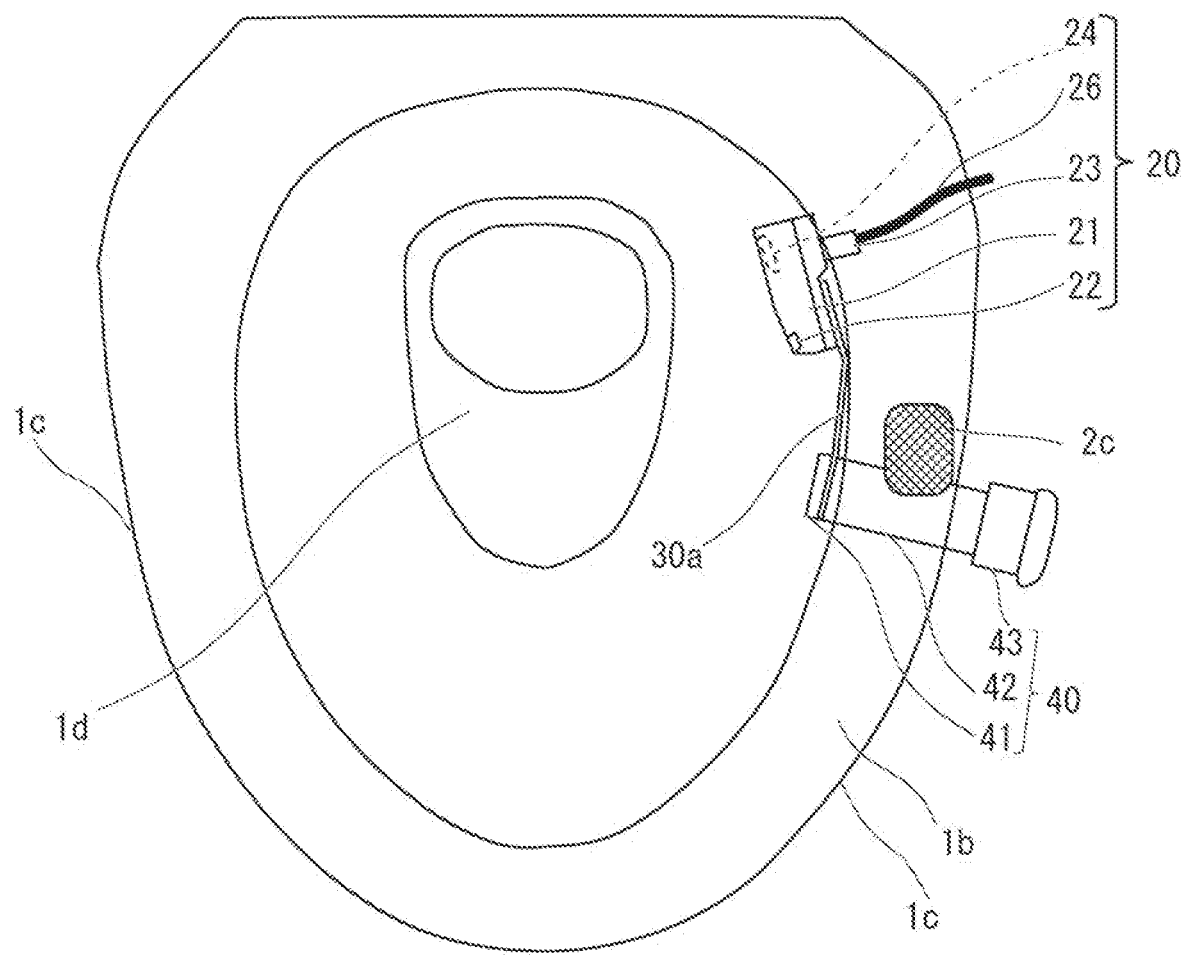
FIG. 7 is a perspective view illustrating a scene in which the information collection apparatus in FIG. 1 is installed in the toilet bowl.

As illustrated in FIG. 7, when the projecting part 2c of the toilet seat 2 interferes with the bridge component 40 at attachment of the sensor box 20 to the toilet bowl 1, the toilet seat and the bridge component 40 may be damaged, and therefore, attachment cannot be performed. While attachment can be performed by shifting the bridge component 40, the sensor box 20 deviates from an optimum fixing position when an amount of shift is, for example, 2 cm or more; and therefore, accurate excretion detection cannot be performed.

Figure 8:
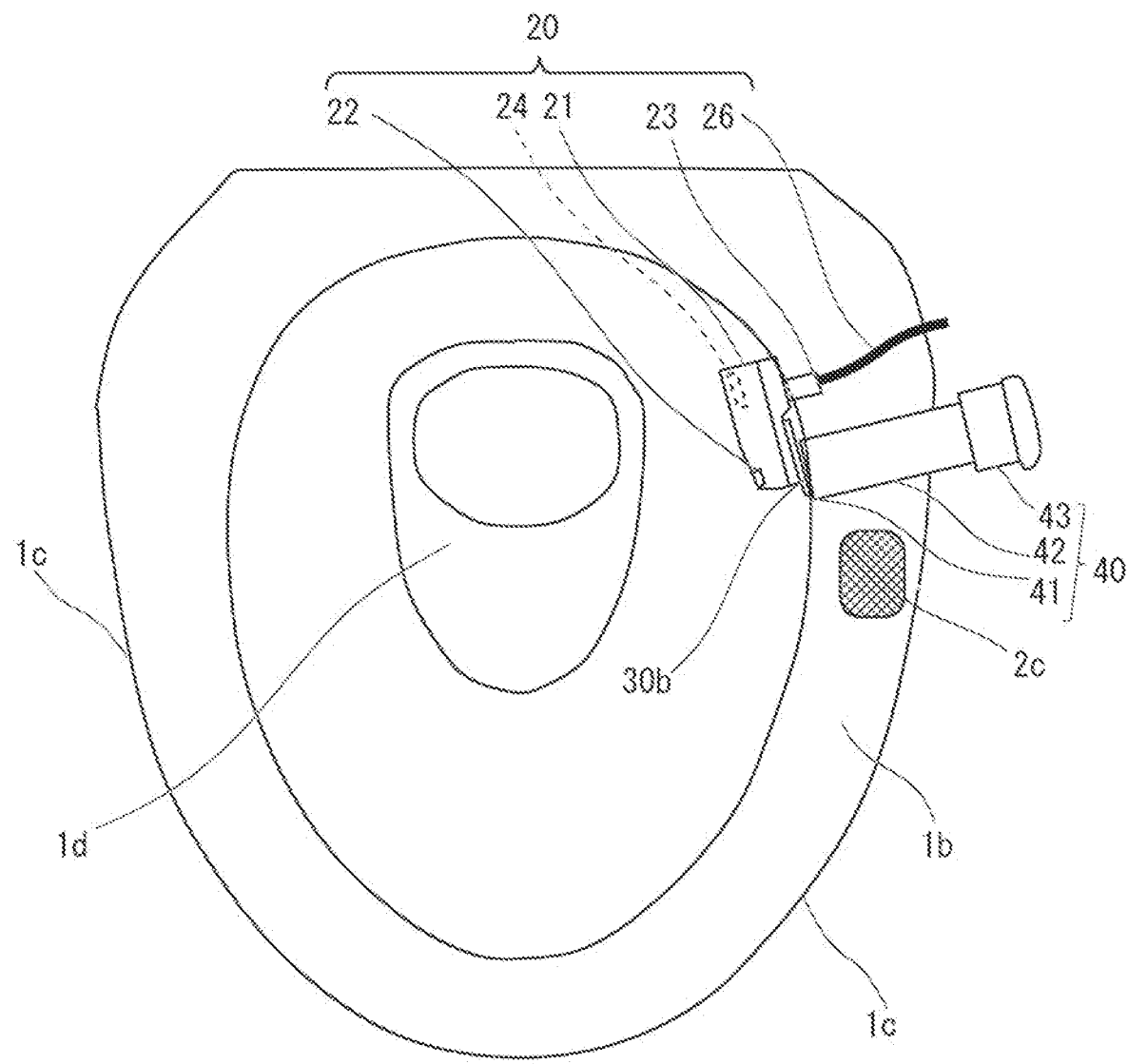
FIG. 8 is a perspective view illustrating a scene in which the information collection apparatus in FIG. 1 is installed in the toilet bowl.

As a countermeasure for avoiding the situation described above, the fitting 30b is attached to the inner housing 21 and the bridge component 40 and is used in place of the fitting 30a, as illustrated in FIG. 8. Thus, the sensor box 20 can be fixed to the optimum position without interference with the projecting part 2c of the toilet seat 2.

Thus, such a structure in which the sensor box 20 and the bridge component 40 are coupled by a selected fitting out of the fittings 30a and 30b enables attachment of the sensor box 20 at an accurate position without interference with the projecting part 1c (the rubber foot part) of the toilet seat 1. Then, by thus enabling installation of the sensor box 20 at an optimum position (a position where information about an excretion including an evacuation at an outlet can be collected), accurate excretion detection and accurate sitting detection can be performed. Further, making the fitting 30 to be used changeable enables accommodation of various types of commercially available toilet seats from major manufacturers.

As described above, the information collection apparatus 10 according to the present example embodiment can be attached to a toilet bowl for any toilet bowl and any toilet seat that are already available and can collect information about an excretion including an evacuation at an outlet. Specifically, the information collection apparatus 10 according to the present example embodiment has a structure enabling attachment while adjusting the aforementioned distance regardless of the shape of the toilet bowl 1, and therefore, the sensor box 20 can be installed at an optimum position in toilet bowls in various shapes. For example, the present example embodiment enables installation of the sensor box 20 at an optimum position without being affected by an environment of a toilet at a home of a person requiring nursing care. Therefore, the present example embodiment enables attachment of the sensor box 20 at an optimum position for toilet bowls in various shapes without the need for increasing the number of types with varying shapes or the like of the information collection apparatus and enables minimization of the administrative cost and the manufacturing cost of the information collection apparatus 10.

Further, as illustrated in FIG. 1, the fitting 30 may be a component attaching the inner housing 21 in such a way that the inner housing 21 is placed at a position located inside the rim 1*c* and located under the toilet seat 2 in the vertical direction when the toilet seat 2 is placed on the top surface of the rim 1*c*. In other words, the entire inner housing 21 or at least the sitting sensor 22 can be attached by the fitting 30 and the bridge component 40 in such as way as to be placed at a position located inside the rim 1*c* and located behind the toilet seat 2 placed on the top surface of the rim 1*c* when viewed from above. The fitting 30 and the bridge component 40 have shapes allowing attachment of such an inner housing 21. Note that while the shape of the inner housing 21 is also not considered relevant in this example, the shape is determined to allow maintenance of the positional relation as described above relative to the toilet seat 2 in consideration of a balance with at least the fitting 30 and the bridge component 40.

By employment of such a placement, the sitting sensor 22 and the information collection unit 24 are placed at positions hidden by the toilet seat 2 and the sensor surfaces in particular are placed at positions hidden by the toilet seat 2, and therefore, cleaning work of the sensor surface of the sitting sensor 22 placed slightly upward can be particularly facilitated. Further, for example, the distance can be changed by the change mechanism in such a way as to accommodate various combinations of a toilet bowl and a toilet seat and achieve such a placement in such a placement example, which is useful.

Further, for example, the present example embodiment can be suitably utilized in the fields of healthcare and medical nursing care in which a structure in which a detection function of an excretion, sitting, and the like is deployed in a toilet bowl in a toilet may be placed.

Second Example Embodiment

Figure 9:
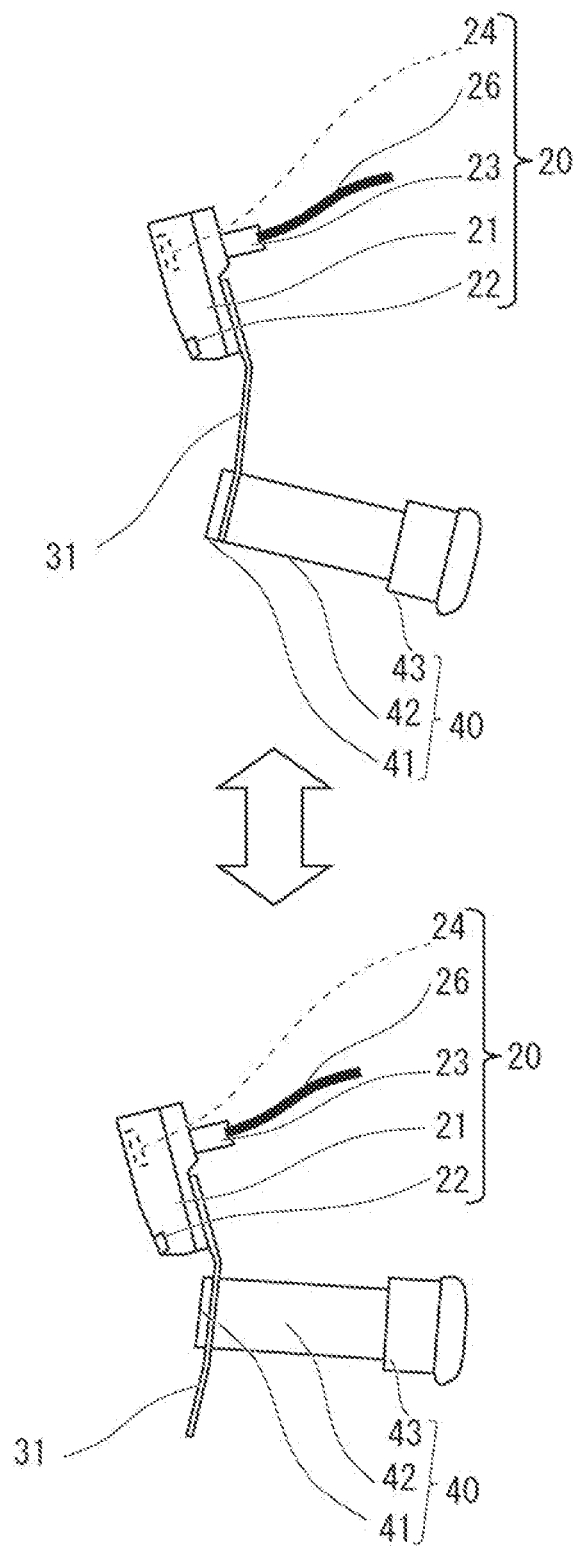
FIG. 9 is a top view illustrating a configuration example of an information collection apparatus according to a second example embodiment.

While a second example embodiment will be described with reference to FIG. 9 with a particular emphasis on the difference between the second example embodiment and the first example embodiment, various examples described in the first example embodiment are applicable. FIG. 9 is a top view illustrating a configuration example of an information collection apparatus according to the second example embodiment.

A change mechanism according to the present example embodiment is a sliding mechanism sliding the position of an inner housing 21 relative to an end 41 in a direction along an inner wall forming the inside of a rim 1*c*. As indicated by the difference between the upper diagram and the lower diagram in FIG. 9, the sliding mechanism may be a mechanism allowing the position of the inner housing 21 relative to the end 41 to slide by, for example, causing a fitting 31 (corresponding to the fitting 30) to pass through the end 41 part in an insertable and removable state. Alternatively, while not being illustrated, the sliding mechanism may be a mechanism sliding the inner housing 21 relative to the fitting 31. Further, configuring the sliding mechanism to allow locking at positions in multiple stages facilitates fixing of the position of a sensor box 20, reduces the possibility of misalignment of the position of the sensor box 20 after installation, and maintains detection precision.

An apparatus attaching method according to the present example embodiment includes a bridge step, a first attachment step, a second attachment step, and a change step as follows. The order of the steps is not considered relevant.

The bridge step bridges the inside of the rim 1*c* of a toilet bowl 1 in a toilet and the outside of the rim 1*c* by placing part of a bridge component 40 on the top surface of the rim 1*c* and sandwiching the rim 1*c* by the bridge component 40. The first attachment step attaches the fitting 31 to the end 41 of the bridge component 40 in a direction of the inside of the rim 1*c*. The second attachment step attaches the inner housing 21 in which a sitting sensor 22 and an information collection unit 24 are placed to the fitting 31. The change step changes, by using the sliding mechanism, the distance from the end 41 to the inner housing 21 in the direction along the inner wall forming the inside of the rim 1*c*.

Further, replacement of a fitting described in the first example embodiment is also applicable to the present example embodiment. For example, preparation of a plurality of fittings 31 with lengths different from each other enables installation with a suitable length according to the length of the fitting 31 and an amount of sliding.

Third Example Embodiment

Figure 10:
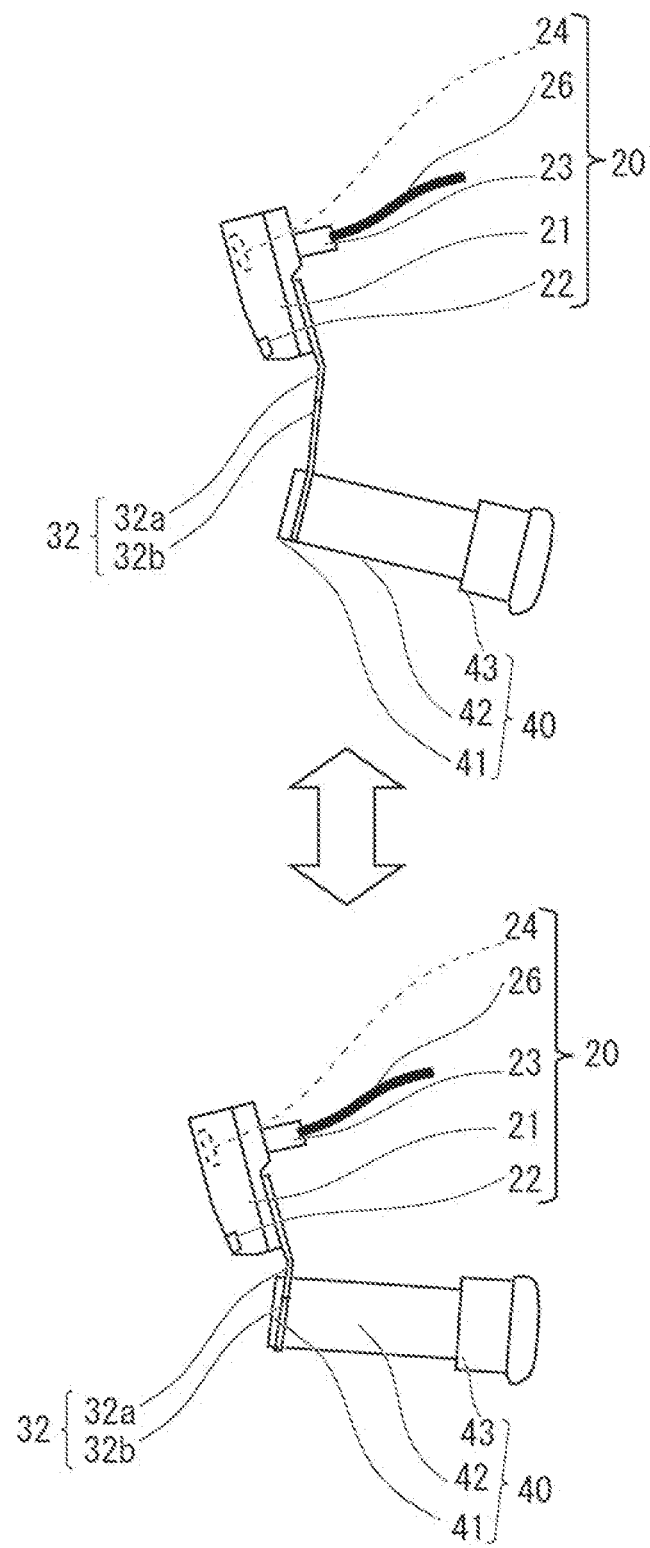
FIG. 10 is a top view illustrating a configuration example of an information collection apparatus according to a third example embodiment.

While a third example embodiment will be described with reference to FIG. 10 with a particular emphasis on the difference between the third example embodiment and the first example embodiment, various examples described in the first and second example embodiments are applicable. FIG. 10 is a top view illustrating a configuration example of an information collection apparatus according to the third example embodiment.

A change mechanism according to the present example embodiment is an extension-shortening mechanism provided in a fitting 32. The extension-shortening mechanism is a mechanism extending and shortening a length in a direction along an inner wall forming the inside of a rim 1*c*. As indicated by the difference between the upper diagram and the lower diagram in FIG. 10, the extension-shortening mechanism provides extension and shortening by constituting the fitting 32 (the fitting 30 provided with an extension and shortening capability) by two members 32*a* and 32*b* and changing the position of the member 32*b* relative to the member 32*a*. For example, the member 32*b* is formed as a tube, the member 32*a* is further formed as a tube with a diameter smaller than that of the member 32*b*, and the member 32a can be fitted into the member 32b. Thus, the length of the fitting 32 can be changed according to the length of the member 32a inserted into the member 32b.

As a matter of course, the shape of the members 32a and 32b is not limited to tubular and has only to be extensible and shortenable as the fitting 32. Further, the fitting 32 may also be constituted by three or more members. Further, configuring the extension-shortening mechanism to allow locking at positions in multiple stages facilitates fixing of the position of a sensor box 20, reduces the possibility of misalignment of the position of the sensor box 20 after installation, and maintains detection precision.

The apparatus attaching method according to the present example embodiment includes a bridge step, a first attachment step, a second attachment step, and a change step as follows. The order of the steps is not considered relevant.

The bridge step bridges the inside of the rim 1c of a toilet bowl 1 in a toilet and the outside of the rim 1c by placing part of a bridge component 40 on the top surface of the rim 1c and sandwiching the rim 1c by the bridge component 40. The first attachment step attaches the fitting 32 to an end 41 of the bridge component 40 in a direction of the inside of the rim 1c. The second attachment step attaches an inner housing 21 in which a sitting sensor 22 and an information collection unit 24 are placed to the fitting 32. The change step changes, by using the extension-shortening mechanism, the distance from the end 41 to the inner housing 21 in the direction along the inner wall forming the inside of the rim 1c.

Further, replacement of a fitting described in the first example embodiment is also applicable to the present example embodiment. For example, preparation of a plurality of fittings 32 with maximum lengths and/or minimum lengths respectively different from each other enables installation with a suitable length according to the length of the fitting 32 and an extended or shortened amount. Furthermore, the sliding mechanism described in the second example embodiment is also applicable to the present example embodiment. For example, additionally providing the sliding mechanism enables installation with a suitable length according to the length of the fitting 32 and an extended or shortened amount.

Fourth Example Embodiment

Figure 11:
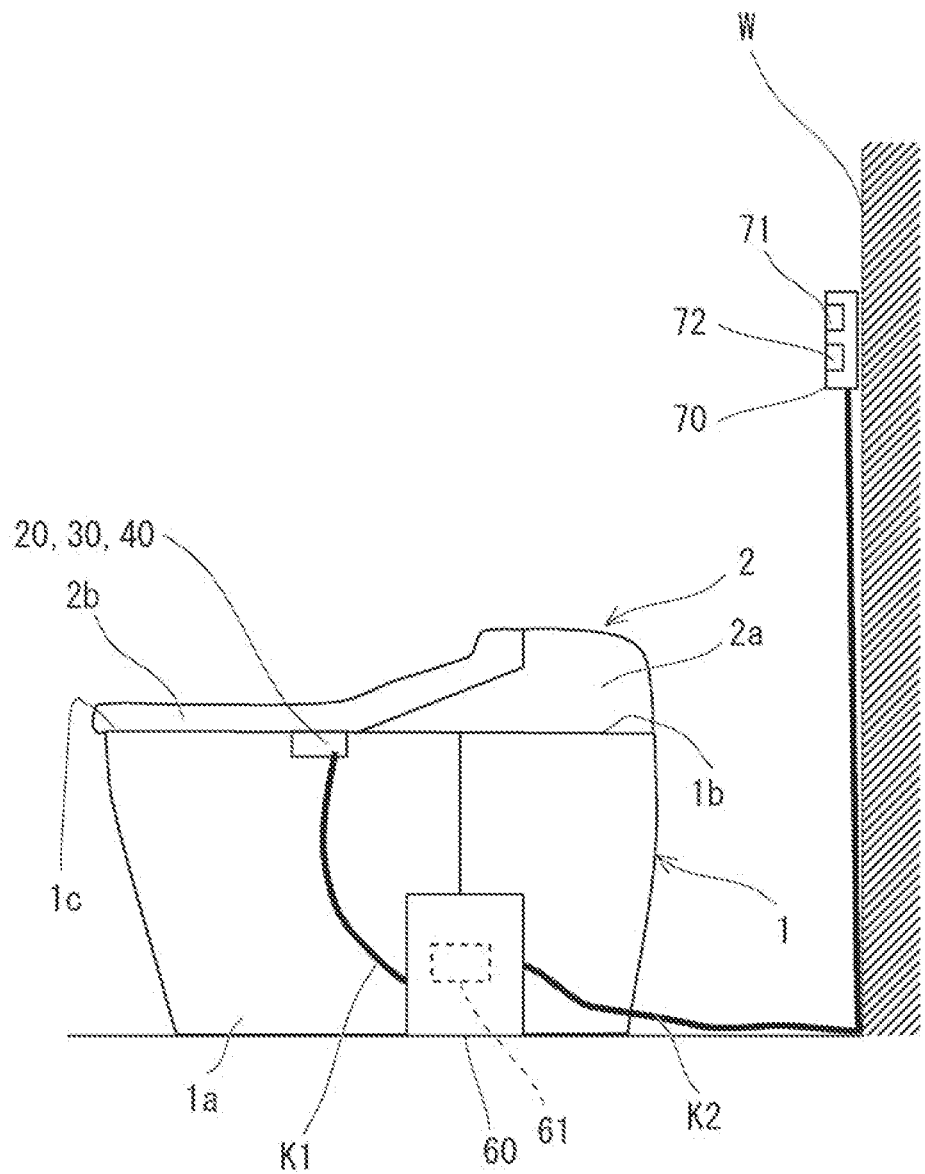
FIG. 11 is a side view illustrating a configuration example of a toilet bowl in which an information collection apparatus according to a fourth example embodiment is installed.

While a fourth example embodiment will be described with reference to FIG. 11 with a particular emphasis on the difference between the fourth example embodiment and the first example embodiment, various examples described in the first to third example embodiments are applicable. FIG. 11 is a side view illustrating a configuration example of a toilet bowl in which an information collection apparatus according to the fourth example embodiment is installed.

The information collection apparatus according to the present example embodiment (hereinafter the present apparatus) is an apparatus acquired by providing a function of distinguishing between users and enabling management of collected excretion information for each user in the information collection apparatus according to the first example embodiment.

As illustrated in FIG. 11, the present apparatus is installed in a distributed manner in or outside a toilet bowl 1, and a sensor box 20 is attached to a rim 1c of the toilet bowl 1 by a fitting 30 and a bridge component 40. The present apparatus may further include a control box 60 including a control unit 61 as the aforementioned control unit, and a human detection/identification box 70 including an image capture apparatus 71 and a human detecting sensor 72. Note that FIG. 11 illustrates an example of a toilet seat 2 not being provided with a lid.

The image capture apparatus 71 is a device capturing an image of the face of a user of a toilet and, for example, may be a camera capturing a static image and/or a dynamic image. Further, without being limited to a visible light camera, the image capture apparatus 71 may be an infrared camera or the like. While, for example, the lens of the image capture apparatus 71 may be exposed from the human detection/identification box 70 in such a way that an image of the face of a user of the toilet can be captured, the device has only to be able to capture an image of the face.

The human detecting sensor 72 may be provided for acquiring a timing for starting the image capture apparatus 71 or capturing an image. The human detecting sensor 72 is a sensor detecting existence of a person (entrance and exit of a person) in a specific region (a measurement area of the human detecting sensor 72); and, for example, an infrared sensor, an ultrasonic sensor, or an optical sensor may be employed regardless of the detection method. While the detection surface of the human detecting sensor 72 may be exposed from the human detection/identification box 70 in such a way that a user of the toilet can be detected, the sensor has only to be able to detect a person.

An information collection unit 24 in the sensor box 20 may be a camera, and the image capture apparatus 71 may also be a camera; and the two will be referred to as a first camera 24 and a second camera 71, respectively, in the following description.

The control box 60 may be a storage housing (part of an outer housing) in which the control unit 61 is stored and may be connected to the sensor box 20 by a cable K1 (a cord 26) and be placed beside a side 1a of the toilet bowl 1.

The control unit 61 controls a sitting sensor 22 and the first camera 24 in the sensor box 20, and the second camera 71 and the human detecting sensor 72 in the human detection/identification box 70. For example, the control unit 61 can receive a detection result by the human detecting sensor 72, can instruct the second camera 71 to capture an image and receive the captured image, and can instruct the first camera 24 to collect information about an excretion and receive the collected information. While an example of the sitting sensor 22, the first camera 24, the human detecting sensor 72, and the second camera 71 being connected to the control unit 61 in a wired manner is given, the components may be connected by wireless communication. Further, a CPU for analyzing information from each sensor and a communication unit for communicating with a server (unillustrated), such as a WiFi (registered trademark, hereinafter the same) interface, may be deployed in the control box 60.

The human detection/identification box 70 may be provided as a separate housing placed outside the outer housing, be connected to the control unit 61 in the control box 60 by a cable K2, and be placed on a wall W of the toilet (a wall located in front when the door of the toilet is opened). As a matter of course, the shapes and the placements of the control box 60 and the human detection/identification box 70 are not limited to those illustrated in FIG. 11, and for example, the control box 60 may be installed behind the toilet bowl 1.

The present apparatus can constitute a system with a wirelessly connected server (unillustrated). Further, the system may include a terminal device (unillustrated) held by an observer of a user of a toilet, the terminal device being wirelessly connected to the server. Note that, for example, the connections may be performed within one wireless local area network (LAN). In this system, recording of an excretion, presentation (such as notification) of excretion information to the terminal device, and excretion prediction can be performed by the present apparatus, the server, and the terminal device in coordination with each other. The recording, the presentation, the prediction, and the like may be achieved by any configuration; and while description is omitted, the present apparatus can function as a toilet installation type recording-notification-excretion prediction system or an apparatus responsible for information collection for the system and may also be referred to as a toilet sensor. Further, the present apparatus may be referred to as an evacuation-urination observation apparatus and may be referred to as an evacuation-urination observation-recording apparatus when further performing information storage.

When detecting a person in a specific region, the human detecting sensor 72 transmits the detection result to the control unit 61. The detection result can be transmitted to the server through the WiFi interface by the control unit 61. Further, receiving the detection result, the control unit 61 can give an image capture instruction to the second camera 71.

The second camera 71 is an example of a camera capturing a facial image of a user of a toilet and acquiring facial image data for user identification and may be installed in such a way as to include the face of a user into an image capture area. The control unit 61 may acquire a human detection result by the human detecting sensor 72 or acquire a result of causing the server to authenticate a user by, for example, capturing an image of the face and instruct the sitting sensor 22 to perform a measurement.

The sitting sensor 22 measures the distance to a target object (the buttocks of a user of the toilet bowl 1) in accordance with an instruction from the control unit 61 or all the time. The control unit 61 acquires the measurement result and when a certain time elapses after a threshold value is exceeded, detects that the target object is sitting on the toilet seat. Further, when the distance to the target object varies after sitting on the toilet seat, the user leaving the toilet seat is detected. The control unit 61 can perform control of instructing the first camera 24 to capture an image in a stage when sitting on the seat is detected and instructing the first camera 24 to end the image capture in a stage when leaving the seat is detected.

The first camera 24 is an example of a camera capturing an image of an excretion and transmitting the captured image data to the control unit 61 and is installed in such a way as to include an excretion area of an excretion in the toilet bowl 1 in the toilet into an image capture area. Note that by providing the human detection/identification box 70 at a location positioned in front when a user sits on the seat, an image of the face can be captured after sitting instead of capturing an image of the face before sitting; and in that case, the human detecting sensor 72 may be omitted.

The control box 60 may include a Bluetooth (registered trademark, hereinafter the same) module. The Bluetooth module is an example of a receiver receiving identification data for user identification from a Bluetooth tag held by a user and may be replaced with a module based on a different short-distance communication standard. A Bluetooth tag held by a user may have an ID varying for each user and, for example, may be held by the user by being embedded in a wristband.

The aforementioned WiFi interface is an example of a communication unit (communication equipment) transmitting various acquired data to the server and may be replaced with a module employing a different communication standard. Facial image data acquired by the second camera 71 and identification data acquired by the Bluetooth module can be transmitted to the server through the WiFi interface by the control unit 61. Further, when a user is detected to be in a sitting state, the control unit 61 may provide notification, through the WiFi interface, to the server or a terminal device of an observer observing the user. Thus, use of the toilet can be notified to the observer, and the observer can be dispatched to the toilet as needed.

The control unit 61 and the server acquire excretion information, based on captured image data captured by the first camera 24. In this case, main processing of acquiring excretion information from the captured image data can be performed by the server. For example, the server inputs the captured image data to a trained model and acquires excretion information. Then, for example, as at least part of the excretion information, the server acquires information indicating whether the captured image data include a foreign matter being an object other than feces and urine as a subject excluding the toilet bowl and a liquid detergent therefor.

The server receives, through the WiFi interface, facial image data acquired by the second camera 71, performs face authentication processing by comparison of, for example, keypoints between the facial image data and prestored authentication data, and acquires identification data associated with matching authentication data. Thus, the server can acquire identification data (identification data for identifying a user), in other words, can specify a user.

Then, in addition to captured image data, the server can acquire, from the present apparatus, facial image data of a user of the toilet bowl 1 when the captured image data are acquired and therefore can identify the user, based on the facial image data, and can manage excretion information for each user in an internal storage device. Further, the server can also generate presentation information for each user. Through the face authentication processing, a most approximate user can be specified as a current user of the toilet. Thus, the aforementioned identification data may be data for identifying a user by executing the face authentication processing, based on facial image data captured by the second camera 71 at the toilet bowl 1 or in a room where the toilet bowl 1 is installed (a toilet cubicle). Note that the facial image data captured by the second camera 71 are preferably not saved in consideration of privacy.

Then, the terminal device can output the presentation information for each user. Further, by predetermining one or a plurality of presentation target persons for each user (such as an observer in charge when the user is a person requiring nursing care), the server can output the presentation information to terminal devices used by the presentation target persons. While examples of an observer include a caregiver, and, depending on circumstances, a doctor, a helper instead of a caregiver may also be included. Further, depending on an application environment of this system, an observer may be a different person.

Furthermore, the server receives, through the WiFi interface, identification data (personal authentication data) acquired by the Bluetooth module and performs user authentication by comparison with prestored identification data for authentication. Note that, for example, when a caregiver holding a Bluetooth tag for the caregiver and a person requiring nursing care holding a Bluetooth tag for the person enter a toilet together, the latter may be selected as a user. Thus, the server can acquire identification data (identification data for identifying a user), in other words, can specify a user.

Then, in addition to captured image data, the server can acquire, from the present apparatus, identification data for identifying a user of the toilet bowl 1 when the captured image data are acquired and therefore can manage excretion information for each user in the internal storage device, based on the identification data. Further, the server can also generate presentation information for each user. Then, the terminal device can output the presentation information for each user. Further, by predetermining one or a plurality of presentation target persons for each user, the server can output the presentation information to terminal devices used by the presentation target persons.

Note that, a user is specified from two types of data being facial image data and identification data, and two specification functions are considered to be provided in this example; however, as a matter of course, user specification can be performed by either one. For example, both specification functions may be provided in this system, and either one may be selected during operation. Alternatively, only either specification function may be provided in this system.

Other Example Embodiments

While the information collection apparatus, the toilet bowl including the apparatus, and the server (server device) along with usage of each have been described in each example embodiment, the above is not limited to those exemplified. For example, the shape of each member in the information collection apparatus, the toilet bowl, and the toilet seat, and a positional relation between the members have only to be able to serve the functions of the members except for the particularly mentioned positional relation. Further, for example, another step may be added to the apparatus attaching method employed in the information collection apparatus.

In the aforementioned example, a program can be stored by using various types of non-transitory computer-readable media and be supplied to a computer. The non-transitory computer-readable media include various types of tangible storage media. Examples of the non-transitory computer-readable medium include magnetic storage media (such as a flexible disk, a magnetic tape, and a hard disk drive), magneto-optical storage media (such as a magneto-optical disk). Furthermore, the examples include a CD-read only memory (ROM), a CD-R, and a CD-R/W. The examples further include semiconductor memories [such as a mask ROM, a programmable ROM (PROM), an erasable PROM (EPROM), a flash ROM, and a random access memory (RAM)]. Further, the program may be supplied to the computer by various types of transitory computer-readable media. Examples of the transitory computer-readable medium include an electric signal, an optical signal, and an electromagnetic wave. The transitory computer-readable medium can supply the program to the computer through wired communication channels such as an electric cable and an optical fiber, or a wireless communication channel.

Note that the present disclosure is not limited to the aforementioned example embodiments and may be modified as appropriate without departing from the scope and spirit of the present disclosure. Further, the present disclosure may be implemented by combining the example embodiments as appropriate.

While the present invention has been described above with reference to the example embodiments, the present invention is not limited to the aforementioned example embodiments. Various changes and modifications that may be understood by a person skilled in the art may be made to the configurations and details of the present invention without departing from the scope of the present invention.

This application claims priority based on Japanese Patent Application No. 2021-140226 filed on Aug. 30, 2021, the disclosure of which is hereby incorporated by reference thereto in its entirety.

REFERENCE SIGNS LIST

1 TOILET BOWL
1a SIDE
1b PLANE PART
1c RIM
1d RESERVOIR PART
1e ATTACHMENT PART
1f WATER TANK
2 TOILET SEAT
2a ATTACHMENT PART
2b TOILET SEAT BODY
2c PROJECTING PART
2f LID
10 INFORMATION COLLECTION APPARATUS (EXCRETION INFORMATION COLLECTION APPARATUS)
20 SENSOR BOX (SENSOR UNIT)
21 HOUSING (INNER HOUSING)
22 SITTING SENSOR
23 PLACEMENT PART
24 INFORMATION COLLECTION UNIT (FIRST CAMERA)
26 CORD
30, 30a, 30b, 31, 32 FITTING
30aa, 30ab, 30bb FIXING PART
32a, 32b MEMBER
40 BRIDGE COMPONENT
41 END (TIP)
41a, 43g ELASTIC MEMBER
42 BRIDGING PART
43 OUTER HOUSING
43a HOUSING BODY
43c SLIDING MEMBER
43d STORAGE PART
43e SLIDE GROOVE
43f DIAL KNOB
60 CONTROL BOX
61 CONTROL UNIT
70 HUMAN DETECTION/IDENTIFICATION BOX
71 IMAGE CAPTURE APPARATUS (SECOND CAMERA)
72 HUMAN DETECTING SENSOR
K1, K2 CABLE

What is claimed is:

1. An information collection apparatus comprising:
a sitting sensor configured to detect that a user of a toilet bowl in a toilet is sitting on a toilet seat placed on a top surface of a rim of the toilet bowl;
information collector configured to collect information about an excretion in the toilet bowl;
a housing in which the information collector and the sitting sensor are placed;
a bridge component configured to bridge an inside of a rim of the toilet bowl and an outside of the rim by placing part of the bridge component on a top surface of the rim and sandwiching the rim;
a fitting configured to be attached to an end of the bridge component in a direction of an inside of the rim and attach the housing; and a change mechanism configured to change a distance from the end to the housing in a direction along an inner wall forming an inside of the rim.

2. The information collection apparatus according to claim 1, wherein the change mechanism is a mechanism fixing the bridge component to the fitting and fixing the housing to the fitting and is a mechanism changing the distance by using, as the fitting to be fixed, a fitting selected from among a plurality of fittings with varying lengths in a direction along the inner wall.

3. The information collection apparatus according to claim 1, wherein the change mechanism includes a sliding mechanism sliding a position of the housing relative to the end in a direction along the inner wall.

4. The information collection apparatus according to claim 1, wherein the change mechanism is an extension-shortening mechanism being provided in the fitting and extending and shortening a length in a direction along the inner wall.

5. The information collection apparatus according to claim 1, wherein the fitting is a jig attaching the housing in such a way that the housing is placed at a position located inside the rim and located under the toilet seat in a vertical direction when the toilet seat is placed on a top surface of the rim.

6. The information collection apparatus according to claim 1, further comprising:
at least one memory storing instructions;
at least one processor configured to execute the instructions to control the sitting sensor and the information collector; and
an outer housing being a housing to be placed outside the toilet bowl, wherein
the at least one memory and the at least one processor are stored in the outer housing.

7. An apparatus attaching method comprising:
bridging an inside of a rim of a toilet bowl in a toilet and an outside of the rim by placing part of a bridge component on a top surface of the rim and sandwiching the rim by the bridge component;
attaching a fitting to an end of the bridge component in a direction of an inside of the rim;
attaching, to the fitting, a housing in which a sitting sensor configured to detect that a user of the toilet bowl is sitting on a toilet seat placed on a top surface of the rim and information collection collector configured to collect information about an excretion in the toilet bowl are placed; and
changing, by using a change mechanism, a distance from the end to the housing in a direction along an inner wall forming an inside of the rim,
wherein the change mechanism is a mechanism fixing the bridge component to the fitting and fixing the housing to the fitting and is a mechanism changing the distance by using, as the fitting to be fixed, a fitting selected from among a plurality of fittings with varying lengths in a direction along the inner wall.

8. An apparatus attaching method comprising:
bridging an inside of a rim of a toilet bowl in a toilet and an outside of the rim by placing part of a bridge component on a top surface of the rim and sandwiching the rim by the bridge component;
attaching a fitting to an end of the bridge component in a direction of an inside of the rim;
attaching, to the fitting, a housing in which a sitting sensor configured to detect that a user of the toilet bowl is sitting on a toilet seat placed on a top surface of the rim and information collector configured to collect information about an excretion in the toilet bowl are placed; and
changing, by using a change mechanism, a distance from the end to the housing in a direction along an inner wall forming an inside of the rim,
wherein the change mechanism is a sliding mechanism sliding a position of the housing relative to the end in a direction along the inner wall.

9. The apparatus attaching method according to claim 7, wherein the fitting is a component attaching the housing in such a way that the housing is placed at a position located inside the rim and located under the toilet seat in a vertical direction when the toilet seat is placed on a top surface of the rim.

10. The apparatus attaching method according to claim 8, wherein the fitting is a component attaching the housing in such a way that the housing is placed at a position located inside the rim and located under the toilet seat in a vertical direction when the toilet seat is placed on a top surface of the rim.

* * * * *